United States Patent [19]

Naumann et al.

[11] Patent Number: 4,968,851
[45] Date of Patent: Nov. 6, 1990

[54] HALOGENOOLEFIN PESTICIDES

[75] Inventors: Klaus Naumann, Leverkusen; Benedikt Becker, Mettmann; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 316,049

[22] Filed: Feb. 24, 1989

Related U.S. Application Data

[62] Division of Ser. No. 47,968, May 8, 1987, Pat. No. 4,839,390.

[30] Foreign Application Priority Data

May 30, 1986 [DE] Fed. Rep. of Germany ....... 3618115

[51] Int. Cl.$^5$ .............................................. C07C 21/18
[52] U.S. Cl. ..................................... 570/136; 570/135
[58] Field of Search ................................ 570/135, 136

[56] References Cited

U.S. PATENT DOCUMENTS

| 2,686,207 | 8/1954 | Crane et al. | 570/136 |
| 4,839,390 | 6/1989 | Naumann et al. | 570/136 |
| 4,876,285 | 10/1989 | Peake | 514/746 |

FOREIGN PATENT DOCUMENTS

| 586215 | 11/1959 | Canada | 570/136 |
| 142926 | 9/1982 | Japan | 570/136 |

OTHER PUBLICATIONS

Hayashi et al., "Chemistry Letters" 1979, pp. 983–986.
Chemical Abstracts, vol. 98, No. 5, Jan. 31, 1983, p. 624.
Chemical Abstracts Service Registry Handbook, 1978 supplement, pp. 803RG, 819RG, 870RG, 882RG, 946RG, 1029RG, 1303RG.
Pesticide Science, vol. 17, Aug. 1986, pp. 441–448, G. G. Briggs et al.

Primary Examiner—J. E. Evans
Attorney, Agent, or Firm—Sprung Horn Kramer & Woods

[57] ABSTRACT

A method of combating arthropods and nematodes which comprises applying thereto, to a habitat thereof or to an area from which they are to be excluded an arthropodicidally or nematocidally effective amount of at least one long-chain halogenoolefine of the formula (I)

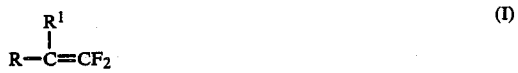

in which
R represents a straight-chain or branched alkyl radical with 8 to 25 carbon atoms in the straight chain, the alkyl radical optionally being interrupted once or several times by a —C≡C— and/or

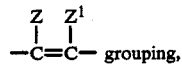

in which
Z and $Z^1$ are identical or different and represent hydrogen or methyl and
$R^1$ represents hydrogen, alkyl or halogen.

Those compounds are new wherein R has at least 12 carbon atoms in the straight chain.

1 Claim, No Drawings

HALOGENOOLEFIN PESTICIDES

This is a division, of application Ser. No. 047,968, filed May 8, 1987, now U.S. Pat. No. 4,839,390.

The invention relates to the use of long-chain halogenoolefines as agents for combating pests, in particular as arthropodicides (preferably insecticides) and nematicides, new long-chain halogenoolefines and processes for their preparation.

It is known that certain unsaturated long-chain carboxylic acid esters, such as for example, B. isopropyl (E,E)-11-methoxy-3,7,1-trimethyl-2,4-dodecanedienoate, can be used as agents for combating pests (Chem. Engng. News 49, No. 29, pages 33-34). Although some long-chain halogenoolefines have been described (compare, for example, C.A. 66, 120597; C.A. 85, 77352n; C.A. 91, 210992e and C.A. 98, 89460u), their possible use as agents for combating pests has not hitherto been disclosed.

It has now been found that the long-chain halogenoolefines of the formula (I)

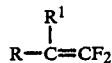  (I)

in which
R represents a straight-chain or branched alkyl radical with 8 to 25 carbon atoms in the straight chain, the alkyl radical optionally being interrupted once or several times by a —C≡C— and/or

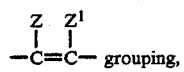 grouping, in which
Z and $Z^1$ are identical or different and represent hydrogen or methyl and
$R^1$ represents hydrogen, alkyl or halogen,
can be used as agents for combating pests, in particular as arthropodicides (preferably insecticides) and nematicides.

The new long-chain halogenoolefines of the formula (Ia)

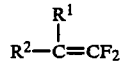  (Ia)

in which
$R^1$ represents hydrogen, alkyl or halogen; and
$R^2$ represents a straight-chain or branched alkyl radical with 12 to 25 carbon atoms in the straight chain, the alkyl radical optionally being interrupted once or several times by a —C≡C— and/or

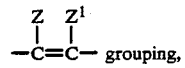 grouping, in which
Z and $Z^1$ are identical or different and represent hydrogen or methyl,
have furthermore been found.

It has moreover been found that the new long-chain halogenoolefines of the formula (Ia) are obtained by a process in which
(a) triphenylphosphonium salts of the formula (II)

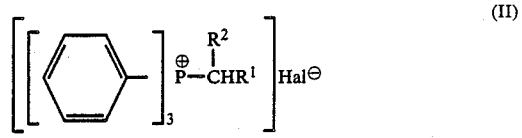  (II)

in which
$R^1$ and $R^2$ have the meanings given above in the case of formula (Ia) and
Hal represents halogen,
are reacted with chlorodifluoromethane in the presence of $C_1$–$C_4$-alkyl-lithium compounds in the presence of inert diluents and in an inert gas atmosphere, or (b) carbonyl derivatives of the formula (III)

  (III)

in which
$R^1$ and $R^2$ have the meanings given above, in the case of formula (Ia),
are reacted with difluoromethanes of the formula (IV)

  (IV)

in which
$X^1$ represents bromine and
$X^2$ represents chlorine or bromine, and with phosphines of the formula (V)

$$PQ_3 \qquad (V)$$

in which
Q represents phenyl or dimethylamino, in the presence of inert diluents and in an inert gas atmosphere.

The compounds of the formula (I) can be prepared by a process analogous to the abovementioned processes for the preparation of the compounds of the formula (Ia) (compare THL 12, 895–898 (1976); Chem. Lett. 1979, 983–986 and THL 23, 2323–2326 (1982)).

The compounds of the formulae (I) and (Ia) have properties which enable them to be used as agents for combating Pests, and in particular they are distinguished by an outstanding arthropodicidal (preferably insecticidal) and nematicidal action.

In the general formulae, R preferably represents straight-chain alkyl with 8 to 25, preferably 10 to 22 and in particular 12 to 20, carbon atoms. The alkyl radical can be interrupted once or several times, preferably once to 6 times, in particular once to 4 times and particularly preferably once or twice, by the —C≡C— group and/or the —C(Z)=C($Z^1$)— group (preferably only by the —C(Z)=C($Z^1$)— group), Z and $Z^1$ preferably being identical and representing hydrogen or methyl. The alkyl radical R which is not interrupted by unsaturated groups is particularly preferred. The radical $R^2$ has the same preferred meaning as the radical R, but alkyl contains 12 to 25, preferably 12 to 22 and in particular 14 to 20 carbon atoms.

Alkyl $R^1$ is straight-chain or branched and preferably contains 1 to 6, in particular 1 to 4, carbon atoms, examples which may be mentioned being methyl, ethyl, n-propyl, i-propyl and n-, i.-, s.- and t.-butyl (preferably methyl and ethyl).

Halogen $R^1$ denotes fluorine, chlorine, bromine or iodine, preferably fluorine, chlorine or bromine and in particular fluorine or chlorine.

In the general formulae, $R^1$ particularly preferably represents hydrogen, methyl or chlorine, especially hydrogen.

Compounds of the formula (I) which are preferably used according to the invention are those in which R represents a straight-chain or branched alkyl radical with 10 to 22 carbon atoms in the straight chain, the alkyl radical optionally being interrupted once to six times by a —C≡C— and/or

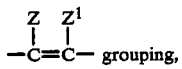  grouping, in which

Z and $Z^1$ are identical or different and represent hydrogen or methyl and $R^1$ represents hydrogen, alkyl with 1 to 6 carbon atoms or fluorine, chlorine or bromine.

Compounds of the formula (I) which are particularly preferably used are those in which R represents a straight-chain or branched alkyl radical with 12 to 20 carbon atoms in a straight chain, the alkyl radical optionally being interrupted once to four times by a

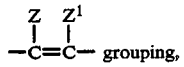 grouping, grouping in which

Z and $Z^1$ are identical or different and represent hydrogen or methyl and $R^1$ represents hydrogen, methyl, ethyl, n-propyl, i-propyl, fluorine or chlorine.

Compounds of the formula (I) which are especially preferred are those in which

R has the particularly preferred meanings given above in the case of formula (I) and $R^1$ represents hydrogen.

Some of the compounds of the formula (I) are new. The compounds of the formula (Ia) are new. Preferred compounds of the formula (Ia) are those in which $R^1$ represents hydrogen, alkyl with 1 to 6 carbon atoms or fluorine, chlorine or bromine and $R^2$ represents a straight-chain or branched alkyl radical with 12 to 22 carbon atoms in the straight chain, the alkyl radical optionally being interrupted once to six times by a —C≡C— and/or

and

Z and $Z^1$ are identical or different and represent hydrogen or methyl.

Particularly preferred new compounds of the formula (Ia) are those in which $R^1$ represents hydrogen, methyl, ethyl, n-propyl, i-propyl, fluorine or chlorine and $R^2$ represents a straight-chain or branched alkyl radical with 14 to 20 carbon atoms in the straight chain, the alkyl radical optionally being interrupted once to four times by a

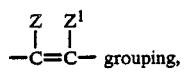 grouping, grouping and Z and $Z^1$ are identical or different and represent hydrogen or methyl.

Especially preferred new compounds of the formula (Ia) are those in which $R^1$ represents hydrogen and $R^2$ has the particularly preferred meanings given above in the case of formula (Ia).

As indicated above R and $R^2$ preferably represent straight-chain alkyl. If R and $R^2$ are branched alkyl each branch contains preferably 1 to 4 and particularly preferred 1 or 2 carbon atoms and represents especially preferred methyl.

If pentadecyl-triphenylphosphonium bromide, chlorodifluoromethane and methyl-lithium are used as starting substances in process variant (a), the course of the reaction can be represented by the following equation:

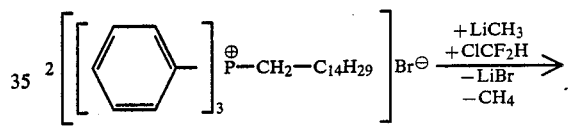

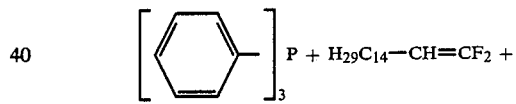

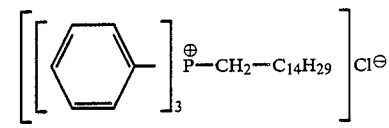

If bromochlorodifluoromethane, pentadecanal and tri(dimethylamino)phosphine are used as starting substances in process variant (b), the course of the reaction can be represented by the following equation:

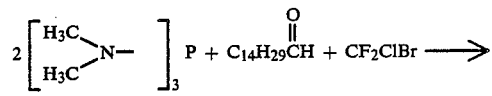

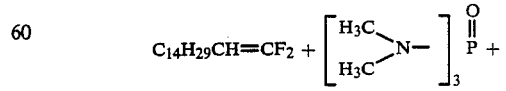

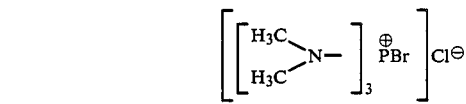

Formula (II) provides a general definition of the triphenylphosphonium salts to be used as starting substances in process (a) according to the invention. In this formula (II), $R^1$ and $R^2$ preferably or particularly preferably represent those radicals which have already been mentioned as preferred or particularly preferred for these substituents in connection with the description of the substances of the formula (Ia) according to the invention. Hal in formula (II) represents halogen, preferably chlorine or bromine.

Examples which may be mentioned of the compounds of the formula (II) are:

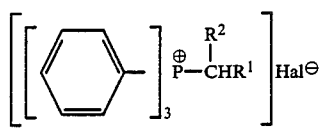

Hal=chlorine or bromine

TABLE 1

| $R^1$ | $R^2$ |
|---|---|
| H | $-C_{12}H_{25}$-n |
| H | $-C_{13}H_{27}$-n |
| H | $-C_{14}H_{29}$-n |
| H | $-C_{15}H_{31}$-n |
| H | $-C_{16}H_{33}$-n |
| H | $-C_{17}H_{35}$-n |
| H | $-C_{18}H_{37}$-n |
| H | $-C_{19}H_{39}$-n |
| H | $-C_{20}H_{41}$-n |
| H | $-C_{21}H_{43}$-n |
| H | $H_3C-\overset{CH_3}{\underset{|}{CH}}-(H_2C)_3-\overset{CH_3}{\underset{|}{CH}}-(CH_2)_3-\overset{CH_3}{\underset{|}{CH}}-(CH_2)_3-\overset{CH_3}{\underset{|}{C}}=CH-$ |
| H | $H_3C-(CH_2)_7-CH=CH-(CH_2)_6-CH_2-$ |
| H | $H_3C-(CH_2)_4-CH=CH-CH_2-CH=CH-(CH_2)_6-CH_2-$ |
| H | $H_3C-(CH_2)_7-CH=CH-(CH_2)_6-CH_2-$ |

The compounds of the formule (II) are known and/or can be prepared in a simple manner by known methods (compare, for example, DE-OS (German Published Specification) 2,551,914; J. Org. Chem. 48, 917–927 and Chem. Ber. 116, 3264–3266).

Formula (III) provides a general definition of the carbonyl derivatives to be used as starting substances in process (b) according to the invention. In this formula (III), $R^1$ and $R^2$ preferably of particularly preferably represent those radicals which have already been mentioned as preferred or particularly preferred for these substituents in connection with the description of the substances of the formula (Ia) according to the invention.

Examples which may be mentioned of the compounds of the formula (III) are:

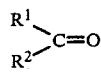

TABLE 2

| $R^1$ | $R^2$ |
|---|---|
| H | $-C_{12}H_{25}$-n |
| H | $-C_{13}H_{27}$-n |
| H | $-C_{14}H_{29}$-n |
| H | $-C_{15}H_{31}$-n |
| H | $-C_{16}H_{33}$-n |

TABLE 2-continued

| $R^1$ | $R^2$ |
|---|---|
| H | $-C_{17}H_{35}$-n |
| H | $-C_{19}H_{39}$-n |
| H | $-C_{20}H_{41}$-n |
| H | $-(H_2C)_8-CH=CH-(CH_2)_6-CH_3$ |
| H | $-(H_2C)_8-CH=CH-CH_2-CH=CH-(CH_2)_4-CH_3$ |
| $CH_3$ | $-C_{12}H_{25}$-n |
| $CH_3$ | $-C_{15}H_{31}$-n |

The carbonyl derivatives of the formula (III) are known or can be prepared in a generally known manner by ozonization of known long-chain terminal olefines or by oxidation of long-chain alcohols.

Formula (IV) provides a general definition of the difluoromethanes also to be used as starting substances in process (b) according to the invention. In this formula (IV), $X^1$ represents bromine and $X^2$ represents chlorine or bromine.

Examples which may be mentioned of the compounds of the formula (IV) are: dibromofluoromethane and bromochlorodifluoromethane.

The compounds of the formula (IV) are known.

Formula (V) provides a general definition of the phosphines furthermore to be used as starting substances in process (b) according to the invention. In this formula, Q represents phenyl or dimethylamino.

Examples which may be mentioned of the phosphines of the formula (V) are: triphenylphosphine and tris-(dimethylamino)-phosphine.

The phosphines of the formula (V) are known compounds of organic chemistry.

Process (a) according to the invention for the preparation of the new long-chain halogenoolefines of the formula (Ia) is preferably carried out using diluents. Possible diluents here are virtually all the inert organic solvents. These include, preferably, ethers, such as diethyl ether, dibutyl ether, glycol dimethyl ether, diglycol dimethyl ether, tetrahydrofuran and dioxane.

Alkyl-lithium compounds which can be employed in process (a) according to the invention are all the alkyl-lithium compounds which can usually be employed for such reactions. Compounds which are preferably suitable are: methyl- and n-butyl-lithium.

The reaction temperatures can be varied within a substantial range in process (a) according to the invention. The reaction is in general carried out at temperatures between −40° C. and +60° C., preferably at temperatures between −20° C. and +30° C.

Process (a) according to the invention is in general carried out under normal pressure. However, it is also possible for the process to be carried out under increased or reduced pressure.

In carrying out process (a) according to the invention, 1.5 to 3.0 mold preferably 2.0 t9 2.6-mol, of alkyl-lithium compound and 1.5 to 3.0 mols preferably 2.0 to 2.6 mols of chlorodifluoromethane are employed per mol of triphenylphosphonium salt of the formula (II). The reaction is carried out in an inert gas atmosphere. Nitrogen is preferably used as the inert gas. Working up is carried out by customary methods.

Process (b) according to the invention for the preparation of the new long-chain halogenoolefines of the formula (Ia) is preferably carried out using diluents. Preferred possible diluents are the solvents which have already been mentioned for process (a) according to the invention.

The reaction temperatures can be varied within a substantial range in process (b) according to the invention.

The reaction is in general carried out at temperatures between −10° C. and +60° C., preferably at temperatures between 0° C. and +30° C.

The process (b) according to the invention is in general carried out under normal pressure. However, it is also possible for the process to be carried out under increased or reduced pressure. An inert gas (advantageously nitrogen) is preferably employed.

In carrying out process (b) according to the invention, 1 to 3.0 mols preferably 2 2 to 2.6 mols, of difluoromethane of the formula (IV) and 2 to 6 mols, preferably 4 to 5 mols of phosphine of the formula (V) are employed per mol of carbonyl derivative of the formula (III). Working up is carried out by customary methods.

The active compounds are suitable for combating animal pests, preferably arthropods and nematodes, in particular insects, encountered in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus, Armadillidium vulgare* and *Porcellio scaber.* From the order of the Diplopoda, for example, *Blaniulus guttulatus* From the order of the Chilopoda, for example, *Geophilus carpophagus* and Scutigera spec. From the order of the Symphyla, for example, *Scutigerella immaculata.* From the order of the Thysanura, for example, Lepisma saccharina. From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Mel-anoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thys:noptera, for example, Hercinothrips femoralis and Thrips tabaci. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus pinlarius, Cheimatobia brumata, Lithocolletis blancardella, Hyponomuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolite sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis and Vespa spp.* From the order of the Diptera, for example, *Aedes spp., Anopheles spp., Culex spp., Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.*

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The compounds of the formula (I) are particularly suitable for combating insects which harm plants, such as, for example, *Plutella maculipennis* and *Spodoptera frugiperda,* and nematodes, such as *Meloidogyne incognita.* They can furthermore be employed in combating soil insects, such as, for example, *Phorbia antiqua* maggots and *Diabrotica balteata.* They are also suitable as development inhibitors for use against, for example, fly maggots. The compounds of the formula (I) or (Ia) are preferably employed in plant protection, the protection of stored products, the protection of materials and for combating insects which are a nuisance in the home and in the industrial field (in particular in plant protection and the protection of stored products).

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seeds and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, Fhalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyehtlene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations according to the invention preferably additionally contain at least one surface-active agent, in addition to at least one active compound of the formulae (I) or (Ia) and at least one extender or carrier.

The formulations in general contain between 0.1 and 95 per cent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds of the formulae (I) and (Ia) are also suitable for combating arthropods, such as insects, mites or ticks, which infest agricultural stock animals, such as, for example, cattle sheep, goats, horses, pigs, donkeys, camels, buffalo, rabbits, chicken, turkeys, ducks, geese and bees, and other pets, such as, for example, dogs, cats, cage birds and aquarium fish, as well as so-called experimental animals, such as, for example, hamsters, guinea pigs, rats and mice.

By combating these arthropods, reductions in output (in meat, milk, wool, hides, eggs, honey and the like), in particular, are to be reduced, so that economic and simple reading of animals is possible by using the active compound.

The active compounds which can be used according to the invention are employed in these sectors in a known manner, by dermal application in the form of, for example, dipping or bathing, spraying, pouring-on and spotting-on, washing and dusting, and with the aid of shaped articles which contain the active compound, such as neck collars, ear tags, tail tags, limb tapes, halters, marking devices and the like.

The active compounds are particularly suitable for combating ectoparasites, such as, for example, *Psoroptes ovis* and *Boophilus microplus*.

The preparation of the active compounds may be illustrated with the aid of the following examples.

PREPARATION EXAMPLES

Example (Ia-1)

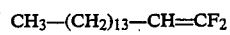

$$CH_3-(CH_2)_{13}-CH=CF_2$$

(Process (a))

190 ml of a 23% strength solution (0.47 mol) of butyl-lithium in n-hexane are added dropwise to a suspension of 240 g (0.43 mol) of pentadecyl-triphenyl-phosphonium bromide in 450 ml of tetrahydrofuran at 0° C. in a nitrogen atmosphere and the mixture is stirred vigorously for 30 minutes. 121 g of a 34% strength solution (0.47 mol) of chlorodifluoromethane in tetrahydrofuran are then added dropwise at 20° C., the mixture is stirred for 8 hours and the same amount of butyl-lithium and chlorodifluoromethane are then added again. The reaction mixture is stirred at 20° C. for about 15 hours. The triphenylphosphine formed is reacted with excess methyl iodide in the reaction mixture. The salt formed is filtered off, the filtrate is concentrated, the residue is taken up in petroleum ether and the mixture is distilled in vacuo.

89 g (80% of theory) of 1,1-difluoro-1-hexadecene of boiling point Bp: 90°–95° C./40 Pa (0.4 mbar) are thus obtained.

TABLE 3

| Example No. | $R^1$ | $R^2$ | Physical constants |
|---|---|---|---|
| Ia-3 | H | $-C_{17}H_{35}$-n | Bp: 82–83° C./ 20 Pa(0.2 mbar) |
| Ia-4 | H | $-C_{13}H_{27}$-n | Bp: 59–60° C./ 25 Pa(0.25 mbar) |
| Ia-5 | H | $-C_{15}H_{31}$-n | Bp: 95° C./ 10 Pa(0.1 mbar) |
| Ia-6 | H | $-(CH_2)_7-CH=CH-(CH_2)_7-CH_3$ | Bp: 100° C./ 10 Pa(0.1 |
| Ia-7 | H | $-(CH_2)_7-CH=CH-CH_2-CH=CH-(CH_2)_4-CH_3$ | Bp: 100° C./ 10 Pa(0.1 mbar) |
| Ia-8 | H | $-C_{19}H_{39}$-n | Bp: 130–133° C./ 10 Pa(0.1 mbar) |
| Ia-9 | H | $-C_{12}H_{25}$-n | Bp: 55–56° C./ 25 Pa(0.25 mbar) |
| Ia-10 | H | $-C_{21}H_{43}$-n | Bp: 140–141° C./ 10 Pa(0.1 mbar) |
| Ia-11 | H | $-C_{18}H_{37}$-n | Bp: 118° C. 8 Pa(0.08 mbar) |
| Ia-12 | H | $-CH=\underset{\underset{CH_3}{\|}}{C}-(CH_2)_3-\underset{\underset{CH_3}{\|}}{CH}-(CH_2)_3-\underset{\underset{CH_3}{\|}}{CH}-(CH_2)_3-\underset{\underset{CH_3}{\|}}{CH}-CH_3$ | Bp: 115–120° C./ 150 Pa(1.5 mbar) |

Example (Ia-2)

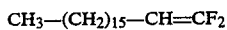

(Process (b))

A solution of 143 g (0.88 mol) of tris-(dimethylamino)-phosphine is added to a solution of 50.8 g (0.2 mol) of heptadecanal and 73 g (0.44 mol) of bromochlorodifluoromethane in 500 ml of tetrahydrofuran at 10° C. in a nitrogen atmosphere. After one hour, a mixture of 27 g (1.5 mols of water and 48 g (1.5 mol) of methanol is added dropwise at a temperature of 0° C. and the aqueous phase is removed. The organic phase is washed with sodium carbonate solution, dilute hydrochloric acid and water. The organic phase is then dried and concentrated. The residue is rectified in vacuo.

37.5 g (65% of theory) of 1,1-difluoro-1-octadecene of boiling point Bp: 99°–100° C./10 Pa (0.1 mbar) are thus obtained.

The following compounds of the formula (Ia) can be prepared analogously to processes (a) and (b) or Example (Ia-1) and (Ia-2):

The compounds of the formula (I) can be prepared analogously to the abovementioned processes (a) and (b) or can be prepared by processes which are known from the literature (compare THL 12, 895–898 (1976); them. Lett. 1979, 983–986 and THL 23, 2323–2326 (1982)):

TABLE 4

| Example No. | $R^1$ | $R^2$ | Physical constants |
|---|---|---|---|
| I-1 | H | $-C_9H_{19}$-n | Bp: 28° C./ 60 Pa(0.6 mbar) |
| I-2 | H | $-C_{11}H_{23}$-n | Bp: 63° C./ 60 Pa(0.6 mbar) |
| I-3 | H | $-C_{10}H_{21}$-n | Bp: 56° C./ 60 Pa(0.6 mbar) |
| I-4 | H | $-CH=\underset{\underset{CH_3}{\|}}{C}-(CH_2)_2-CH=\underset{\underset{CH_3}{\|}}{C}-(CH_2)_2-CH=\underset{\underset{CH_3}{\|}}{C}-CH_3$ | Bp: 105° C./ 40 Pa(0.4 mbar) |
| I-5 | $CH_3$ | $-C_{10}H_{21}$-n | Bp: 107–108° C./ 2000 Pa(20 mbar) |

The activity of the compounds of the formulae (I) and (Ia) may be illustrated with the aid of the following examples:

Example A

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (Plutella maculipennis), as long as the leaves are still moist.

After the specified period of time, the destruction in % is determined.

In this test, for example, the compounds from preparation Examples (Ia-1), (Ia-2), (Ia-3), (Ia-5), (Ia-6), (Ia-7) and (Ia-9) showed an activity of 100% after 3 days at an active compound concentration of 0.1%.

Example B

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Spodoptera frugiperda*), as long as the leaves are still moist.

After the specified period of time, the destruction in % is determined.

In this test, for example, the compounds from preparation Examples (Ia-1), (IA-2), (Ia-7), and (Ia-9) showed an action of 100% after 3 days at an active compound concentration of 0.1%.

Example C

Test insect: *Phorbia antiqua* maggots in the soil

Solvent: 3 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects.

In this test, for example, the compounds from preparation Examples (Ia-1) and (Ia-2) showed a destruction of 100% at an active compound concentration of 10 ppm.

Example D

Test insect: *Diabrotica balteata*—lavae in the soil

Solvent: 3 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects.

In this test, for example, the compounds from preparation Examples (Ia-1) and (Ia-2) showed a destruction of 100% at an active compound concentration of 20 ppm.

Example E

Test nematode: *Meloidogyne incognita*

Solvent: 3 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, potatoes are planted and the pots are kept at a greenhouse temperature of 18° C.

After six weeks, the potato roots are examined for cysts and the degree of effectiveness of the active compound is determined in %.

In this test, for example, the compounds from preparation Examples (la-1) and (IA-2) showed 100% freedom from cysts at an active compound concentration of 20 ppm Example F Fly maggot development-inhibiting test Test insects: *Musca domestica* (multi-resistant)

Solvent: Acetone 2 parts by weight of active compound are taken up in 1,000 parts by volume of solvent. The solution thus obtained is diluted to the desired concentrations with further solvents.

2.5 ml of active compound solution are pipetted into a Petri dish. On the bottom of the Petri dish is a filter paper with a diameter of about 9.5 cm. The Petri dish remains open until the solvent has completely evaporated. The amount of active compound per m² of filter paper varies according to the concentration of the active compound solution. About 25 test insects are then introduced into the Petri dish and the dish is covered with a glass lid.

14 days after the experiments have been set up, the number of flies which have hatched is checked.

In this test, for example, the compounds from preparation Examples (Ia-1) and (Ia-2) showed an inhibition of hatching of 100% at an active compound concentration of 0.02%.

Example G

Test with *Boophilus microplus* resistant

| Solvent: | 35 parts by weight of ethylene glycol monomethyl ether |
| | 35 parts by weight of nonylphenol polyglycol ether |

To produce a suitable preparation of active compound, three parts by weight of active compound are mixed with seven parts by weight of the solvent mixture indicated above, and the concentrate this obtained is diluted with water to the desired concentration.

10 adult Boophilus microplus res. are immersed for 1 minute in the active compound preparation to be tested. After transfer to plastic beakers and storage in a climatically controlled chamber, the degree of destruction is determined.

In this test, for example, the compounds from preparation Examples (Ia-1), (Ia-7), (Ia-9) and (I-3) showed an activity of 100% at an active compound concentration of 10000 ppm.

Example H

Test with *Psoroptes ovis*

| Solvent: | 35 parts by weight of ethylene glycol monomethyl ether |
| | 35 parts by weight of nonylphenol polyglycol ether |

To produce a suitable preparation of active compound, three parts by weight of active compound are mixed with seven parts by weight of the abovementioned solvent mixture and the concentrate thus obtained is diluted with water to the desired concentration.

About 10–25 Psoroptes ovis are introduced into 1 ml of the active compound preparation to be tested, this having been pipetted into tablet nests of a deep-drawn package.

In this test, for example, the compounds from preparation Examples (Ia-4) and (I-3) showed a destruction of 100% at an active compound concentration of 10 ppm.

It will be understood that the specification and examples are illustrative but not limitative of the present invention and that other embodiments within the spirit and scope of the invention will suggest themselves to those skilled in the art.

What is claimed is:

1. 1,1-Difluoro-1-nonadecene of the formula $$CH_3-(CH_2)_7-CH=CH-(CH_2)_7-CH=CF_2.$$

* * * * *

UNITED STATES PATENT AND TRADEMARK OFFICE
CERTIFICATE OF CORRECTION

PATENT NO. : 4,968,851

DATED : November 6, 1990

INVENTOR(S) : Naumann et al.

It is certified that error appears in the above-identified patent and that said Letters Patent is hereby corrected as shown below:

Col. 16, claim 1   Delete " $CH_3-(CH_2)_7=CH-CH-(CH_2)_7-CH=CF_2$. " and
line 2             substitute -- $CH_3-(CH_2)_7-CH=CH-(CH_2)_7-CH=CF_2$. --

Signed and Sealed this

Twenty-seventh Day of October, 1992

Attest:

DOUGLAS B. COMER

Attesting Officer    Acting Commissioner of Patents and Trademarks